United States Patent
Cho et al.

(10) Patent No.: US 7,364,857 B2
(45) Date of Patent: Apr. 29, 2008

(54) METHOD OF PURIFYING NUCLEIC ACID USING SILVER NANOPARTICLES

(75) Inventors: Yoon-kyoung Cho, Gyeonggi-do (KR); Sook-young Kim, Gyeonggi-do (KR); Jin-tae Kim, Gyeonggi-do (KR); Kyu-sang Lee, Gyeonggi-do (KR)

(73) Assignee: Samsung Electronics Co., Ltd (KR)

( * ) Notice: Subject to any disclaimer, the term of this patent is extended or adjusted under 35 U.S.C. 154(b) by 184 days.

(21) Appl. No.: 11/257,833

(22) Filed: Oct. 25, 2005

(65) Prior Publication Data
US 2006/0240408 A1    Oct. 26, 2006

(30) Foreign Application Priority Data
Nov. 25, 2004    (KR) ...................... 10-2004-0097595

(51) Int. Cl.
*C12Q 1/68*    (2006.01)

(52) U.S. Cl. ......................................................... 435/6

(58) Field of Classification Search ..................... None
See application file for complete search history.

(56) References Cited

U.S. PATENT DOCUMENTS

| 5,234,809 A | 8/1993 | Boom et al. | |
|---|---|---|---|
| 2004/0219361 A1* | 11/2004 | Cui et al. ................. | 428/402.2 |

OTHER PUBLICATIONS

Tokareva et al., "Hybridization of Oligonucleotide-Modified Silver and Gold Nanoparticles in Aqueous Dispersions and on Gold Films," JACS, 2004, vol. 126, pp. 15784-15789.*
DeAngelis et al., "Solid-phase reversible immobilization for the isolation of PCR products," *Nucleic Acids Research* (1995) 23(22): 4742-4743.

* cited by examiner

*Primary Examiner*—Young J. Kim
(74) *Attorney, Agent, or Firm*—Cantor Colburn LLP

(57) ABSTRACT

Provided is a method of purifying a target substance using silver nanoparticles. The method includes: mixing a sample containing molecules having a thiol group with the silver nanoparticles to obtain a complex of the molecules having the thiol group with the silver nanoparticles; and isolating and removing the complex from the mixture. By using the purification method, PCR amplifiable DNAs can be rapidly purified, and thus, the method can be very efficiently applied to lab-on-chip (LOC).

9 Claims, 2 Drawing Sheets

SEQUENCE LISTING

```
<160> NUMBER OF SEQ ID NOS: 4

<210> SEQ ID NO 1
<211> LENGTH: 19
<212> TYPE: DNA
<213> ORGANISM: Artificial
<220> FEATURE:
<223> OTHER INFORMATION: Forward primer

<400> SEQUENCE: 1
agtgtggatt cgcactcct                                                    19

<210> SEQ ID NO 2
<211> LENGTH: 23
<212> TYPE: DNA
<213> ORGANISM: Artificial
<220> FEATURE:
<223> OTHER INFORMATION: reverse primer

<400> SEQUENCE: 2
gagttcttct tctaggggac ctg                                               23

<210> SEQ ID NO 3
<211> LENGTH: 21
<212> TYPE: DNA
<213> ORGANISM: Artificial
<220> FEATURE:
<223> OTHER INFORMATION: reverse primer

<400> SEQUENCE: 3
yccakactcc atacgggagg c                                                 21

<210> SEQ ID NO 4
<211> LENGTH: 19
<212> TYPE: DNA
```

```
<213> ORGANISM: Artificial
<220> FEATURE:
<223> OTHER INFORMATION: Reverse primer

<400> SEQUENCE: 4
gatttaccgc rrctggcac                                                   19
```

METHOD OF PURIFYING NUCLEIC ACID USING SILVER NANOPARTICLES

CROSS-REFERENCE TO RELATED PATENT APPLICATION

This application claims the benefit of Korean Patent Application No. 10-2004-0097595, filed on Nov. 25, 2004, in the Korean Intellectual Property Office, the disclosure of which is incorporated herein in its entirety by reference.

BACKGROUND OF THE INVENTION

1. Field of the Invention

The present invention relates to a method of purifying nucleic acids using silver nanoparticles.

2. Description of the Related Art

The production of high purity double-strand plasmid DNAs, single-strand phage DNAs, chromosomal DNAs, and agarose gel-purified DNA fragments is very important in molecular biology. Ideal methods of purifying DNAs should be simple and can be performed rapidly and include little additional manipulation of samples. The DNAs obtained using such methods are ready for direct transformation, restriction enzyme analysis, ligation, or sequencing. Such methods are very attractive in the automated production of DNA samples, which is favored in research and diagnosis labs. Generally, the preparation of plasmid DNAs from crude alcohol precipitates is laborious. Plasmid DNAs are often produced using a CsCl gradient, gel filtration, ion exchange chromatography, RNAase, proteinase K, and repeated alcohol precipitation. These methods require considerable downstream sample preparation to remove CsCl and other salts, EtBr, and alcohol, etc. Further, small negatively charged cellular components can be precipitated together with DNAs. Thus, the DNAs may be contaminated to an undesirable degree.

Methods of purifying nucleic acids using solid phase materials are well known in the art. For example, U.S. Pat. No. 5,234,809 describes a method of purifying a nucleic acid using a solid phase material which can bind to the nucleic acid. Specifically, the method includes mixing a chaotropic material with a nucleic acid binding solid phase, separating the solid phase material with the nucleic acid bound thereto from the liquid, and washing the solid phase material-nucleic acid complexes. Examples of the chaotropic material include guanidinium thiocyanate (GuSCN), guanidine hydrochloride (GuHCl), sodium iodide (NaI), potassium iodide (KI), sodium thiocyanate (NaSCN), urea, and combinations thereof. Examples of the solid phase material include silica particles.

However, this method is considerably time-consuming, complicated, and unsuitable for lab-on-a-chip (LOC). Further, this method uses the chaotropic material as an essential component. If the chaotropic material is not used, nucleic acid cannot bind to the solid phase material. Since the chaotropic material is harmful to a human body, it must be carefully handled. In addition, the chaotropic material inhibits a subsequent process, such as PCR (polymerase chain reaction), and thus, it must be removed from the nucleic acid during or after purification of the nucleic acid.

Research has been conducted to develop a solid phase material having a large surface area for efficient binding with a nucleic acid. However, a method of purifying a nucleic acid using the solid phase material still requires many treatment processes and the use of chaotropic salts and is time-consuming.

A reversible immobilization method using a solid phase material has been described [Hawkins, et al., Nucleic Acids Res. 1995; 23:22]. This method is a simple method and easily automated. However, the application of this method to the detection of pathogens has not been described and this method is not suitable for the production of LOC.

There have been reported kits for producing single tube samples, which are available from GeneReleaser (manufactured by Bioventures), ReleaseIT (manufactured by CPG Inc.), and Lye-N-Go™ RCR Reagent (manufactured by Pierce). By using the kits, samples can be prepared in only two steps and PCR samples can be prepared within 10-15 minutes. However, areal-time PCR cannot be performed due to the use of a white polymer reagent and after cell lysis, reagents and a PCR mixture must be added, which is inconvenient and results in possible contamination of the samples.

The present inventors conducted research on a method of purifying a nucleic acid based on the general techniques and discovered that silver nanoparticles can bind to a molecule having a thiol group in a sample, and can then be removed from the sample using a SH-modified membrane.

SUMMARY OF THE INVENTION

The present invention provides a method of efficiently purifying a nucleic acid using silver nanoparticles in a short time.

According to an aspect of the present invention, there is provided a method of purifying a target substance using silver nanoparticles, comprising: mixing a sample containing molecules having a thiol group with the silver nanoparticles to obtain a complex of the molecules having the thiol group with the silver nanoparticles; and isolating and removing the complex from the mixture.

The sample may comprise a cell or a virus and the method may further comprise lysing the cell or the virus.

The target substance may be a nucleic acid or a sugar.

The lysing of the cell or the virus may be performed using a method selected from the group consisting of mechanical grinding, a method using a chemical reaction, a method using an electrochemical reaction, a method using a biochemical substance, a method using ultrasonic waves, a method using sound waves, a method using microwaves, heating, a method using a laser, a method using electric field, and electrolysis.

The silver nanoparticle complex may be removed by passing the mixture through a structure having SH groups.

The structure having SH groups may be a glass fiber membrane modified with 3-(mercaptopropyl)trimethoxysilane.

The silver nanoparticles may have a size of 1-100 nm.

The concentration of the silver nanoparticles may be 10-1000 ppm, preferably 100-1000 ppm.

The silver nanoparticles may be directly added to the sample or generated by electrolysis using a silver electrode.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Hereinafter, the present invention will be described in more detail step by step.

According to an embodiment of the present invention, there is provided a method of purifying a target substance using silver nanoparticles, comprising:

mixing a sample containing molecules having a thiol group with the silver nanoparticles to obtain a complex of the molecules having the thiol group with the silver nanoparticles; and isolating and removing the complex from the mixture.

Figure 1:
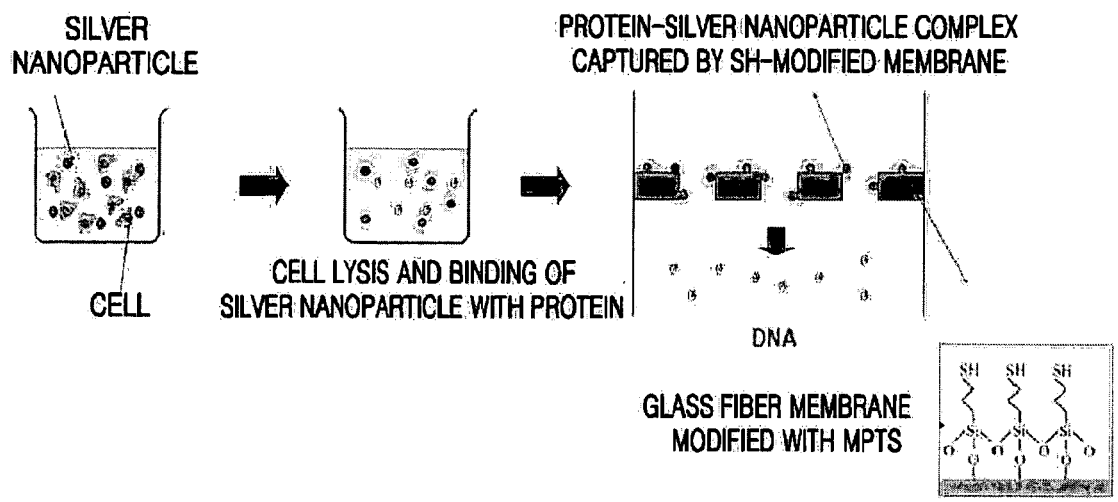
FIG. 1 is a flow diagram illustrating a method of purifying a nucleic acid using silver nanoparticles according to an embodiment of the present invention.

FIG. 1 is a flow diagram illustrating a method of purifying a nucleic acid using silver nanoparticles according to an embodiment of the present invention. Referring to FIG. 1, first, cells and silver nanoparticles are mixed in a container. Then, cells are lysed using boiling or microwave treatment, or a similar method. Once the cell are lysed, the silver nanoparticles bind to proteins. The proteins are modified during the cell lysis, thereby exposing the thiol groups, which allows the silver nanoparticles to bind to the thiol groups of the proteins. It is assumed that bonds between the silver nanoparticles and the proteins are formed via thiol groups in cysteine and methionine of the proteins. The bonds between the silver nanoparticles and the thiol groups are very strong, irreversible, and covalent. Next, the obtained protein-silver nanoparticle complexes are filtered through a SH-modified membrane. At this time, most proteins are removed from the cell lysate and DNAs remain in the solution. Thus, a PCR amplification can be facilitated using the resultant DNA solution.

According to an embodiment of the present invention, the target substance is a nucleic acid or a sugar. The target substance may be any substance not having a thiol group, and preferably a nucleic acid for realizing LOC.

According to an embodiment of the present invention, the lysing of a cell or a virus may be performed using a method selected from the group consisting of mechanical grinding, a method using a chemical reaction, a method using an electrochemical reaction, a method using a biochemical substance such as enzyme, a method using ultrasonic waves, a method using sound waves, a method using microwaves, heating, a method using a laser, a method using electric field, and electrolysis. The cell lysis method using the cells to which the silver nanoparticles are added barely affects the PCR results.

According to an embodiment of the present invention, the protein-silver nanoparticle complex is isolated from the sample through a SH-modified membrane. The SH-modified membrane may be any material modified with a thiol group, and is preferably glass fiber membrane modified with 3-(mercaptopropyl)trimethoxysilane.

According to an embodiment of the present invention, the silver nanoparticles may have a size of 1-100 nm. If the size of the silver nanoparticles is greater than 100 nm, the efficiency of the binding of silver nanoparticles to proteins can be low. If the size of the silver nanoparticles is less than 1 nm, the silver nanoparticles cannot be easily manufactured.

According to an embodiment of the present invention, the concentration of the silver nanoparticles may be 10-1000 ppm, preferably 100-1000 ppm. If the concentration of the silver nanoparticles is less than 100 ppm, the proteins cannot be removed from the sample. If the concentration of the silver nanoparticle is greater than 1000 ppm, the PCR amplification is not well facilitated, even after the SH filtration. That is, when the concentration of the silver nanoparticles is too high, the PCR amplification cannot be performed although a large amount of the modified protein can be removed from the sample. If the concentration of the silver nanoparticles is 100 ppm or less, the PCR is not inhibited regardless of whether the SH filtration has been performed. Further, the results of the PCR are not affected if the concentration of the silver nanoparticles is 10 ppm or less. By using a plurality of membranes or increasing the surface area of the membrane in the SH filtration apparatus, the maximum concentration of the silver nanoparticles at which PCR amplification is not affected can be increased.

According to an embodiment of the present invention, the silver nanoparticles are directly added to the sample or generated by electrolysis using a silver electrode.

Hereinafter, the present invention will be described in more detail with reference to the following examples. The examples are provided for the purpose of illustration and are not intended to limit the scope of the invention.

EXAMPLES

Example 1

Inhibition Effect of Silver Nanoparticles on PCR Amplification

In Example 1, to confirm an inhibition effect of silver nanoparticles on PCR amplification, the PCR was performed while varying the concentration of the silver nanoparticles and the concentration of the silver nanoparticles at which the PCR was not inhibited was determined.

$10^5$ copies/μl of HBV plasmid DNAs were two-fold diluted with silver nanoparticle solutions having concentrations of 0.1, 1, 10, 100, 1000 ppm (serially diluted with ultra-pure water) (cells: silver nanoparticles=250 ul: 250 ul). The prepared samples were subjected to real-time PCRs (TMC1000), both with SH filtration to remove the silver nanoparticles and without SH filtration.

Isolation of the silver nanoparticles using the SH filtration was carried out by dispensing 500 μl of the mixed solution of HBV plasmid DNAs and the silver nanoparticles into an SH filter and centrifuging the obtained filtrate at 13,000 rpm for 3 minutes within 1 minute after the filtration to collect the supernatant.

The results were confirmed by determining a cycle of threshold (Ct) value and a concentration of the PCR product (ng/μl). The Ct value refers to the number of cycles at which a detectable fluorescent signal is generated in a real-time PCR. When an initial DNA concentration is high, the amplification is large and thus a fluorescent signal is detectable with a small number of cycles. That is, as the initial DNA concentration increases, the Ct decreases. The Ct value is also related to DNA purity. As the DNA purity increases, the Ct value decreases. That is, a lower Ct value implies that the purity of the DNAs in the solution is high.

Figure 2:
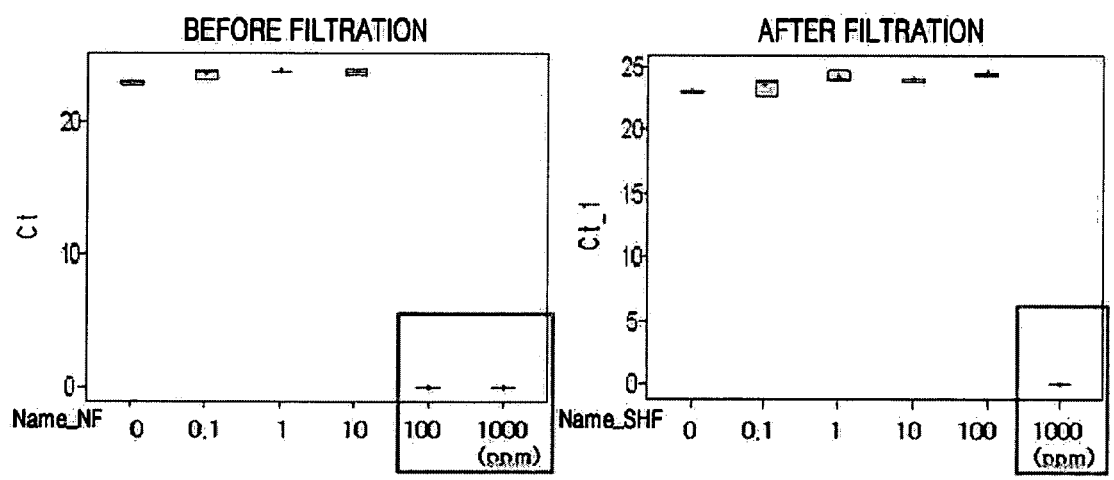
FIG. 2 illustrates graphs showing the cycle of threshold (Ct) value vs. the concentration of silver nanoparticles in polymerase chain reactions (PCRs)

FIG. 2 illustrates graphs of the Ct value vs. the concentration of silver nanoparticle in PCRs before and after filtration, respectively. In both cases, silver nanoparticles with a concentration of 10 ppm or less did not affect the PCR. Without the SH filtration, the PCR did not occur at 100 ppm or more of the silver nanoparticles. With the SH filtration, the PCR did not occur at 1000 ppm or more of the silver nanoparticles. This shows that when the SH filtration was carried out, the concentration of the silver nanoparticles was reduced from 100 ppm to 10 ppm or less. Thus, when the SH filtration is not performed, the concentration of silver nanoparticle must be 10 ppm or less, and when the SH filtration is to be performed, the concentration of silver nanoparticle may be 100 ppm or less.

By using a plurality of membranes or increasing the surface area of the membrane in the SH filtration apparatus, the concentration of the silver nanoparticles at which PCR amplification is not affected can be increased up to 1000 ppm.

Example 2

Removal of Silver Nanoparticle Complexes Using SH-Modified Membrane

To confirm whether an SH-modified membrane can remove silver nanoparticle complexes, concentrations of the silver nanoparticles before and after SH filtration were measured. An SH-modified glass fiber membrane was prepared by binding 53.8 mM 3-(mercaptopropyl)trimethoxysilane (MPTS) in isopropanol to a glass fiber membrane at room temperature, washing the membrane twice with isopropanol, drying the washed membrane in an oven at 80° C. for 5 minutes, and then washing the dried membrane with distilled water. A 100 ppm silver nanoparticle solution (1/10 dilution of NANOVER™ colloidal solution) was filtered through the SH-modified glass fiber membrane and the concentrations of the silver nanoparticles before and after the SH filtration were measured using an Inductively Coupled Plasma Atomic Emission Spectrophotometer (ICP). The concentrations of the silver nanoparticles before and after the SH filtration were 24.1 ppm and 0.0022 ppm, respectively. Thus, it was confirmed that 100 ppm of silver nanoparticles were almost completely removed from the solution using the SH membrane filter.

Example 3

Purification of Nucleic Acid of *E. coli* Cell Using Silver Nanoparticles and Sound Waves To confirm whether a purification method according to an embodiment of the present invention can be applied to manufacturing samples for detecting *E. coli*, nucleic acids were purified from *E. coli* cells using a purification method according to an embodiment of the present invention and subjected to PCRs.

*E. coli* strain BL2 cells having recombinant hepatitis B virus (rHBV) (STRATAGENE) were cultured in an LB medium (Sambrook et al., 1989) at 37° C. in an aerobic condition until log phase ($OD_{600}$=1.5). The bacteria cells were collected by centrifugation and washed twice with 3 ml of phosphate buffered saline (PBS). Then, the cells were resuspended in PBS (cell density: $1 \times 10^6$ cells/ml).

Cell lysis was monitored and to detect DNAs released from the lysed cells, a pair of PCR primers, primer A (SEQ ID No. 1) and primer B (SEQ ID No. 2), were used. The primers A and B are complementary to respective ends of a gene coding HBV nucleic acid. The PCR was performed on a silicon-glass micro PCR chip using a total volume of 1 μl of a reaction mixture containing the following components: 1×SYBR Green PCR buffer (PE Biosystems), 1 mM each of forward and reverse primers (Genotech, Korea), 200 μM each of dNTPs (Sigma), 5 mM $MgCl_2$(Sigma), 5% glycerol (Sigma), 500 mM formamide (Promega), 0.2 ng/μl BSA (Sigma), and 0.1 unit/μl Taq polymerase (SolGent. Co, Ltd, Korea).

Real-time monitoring of PCR amplification was carried out using a newly developed GenSpector® TMC-1 000 system. The conditions of the PCR amplification were as follows: pre-denaturation at 91° C. for 1 minute and 40 cycles with each cycle including denaturation at 92° C. for 1 sec and annealing and extension at 62° C. for 15 sec. After the amplification cycles, the sample was heated slowly from 60° C. to 90° C. (0.1° C./sec) and a melting curve was obtained. It took a total of less than 25 minutes to carry out 40 cycles of the amplification and melting analysis. To confirm whether the real-time PCR was successfully performed, the amplified PCR products were subjected to electrophoresis using an Agilent 2100 Bioanalyzer (Palo Alto, Calif.) together with a DNA 500 assay kit.

Figure 3:
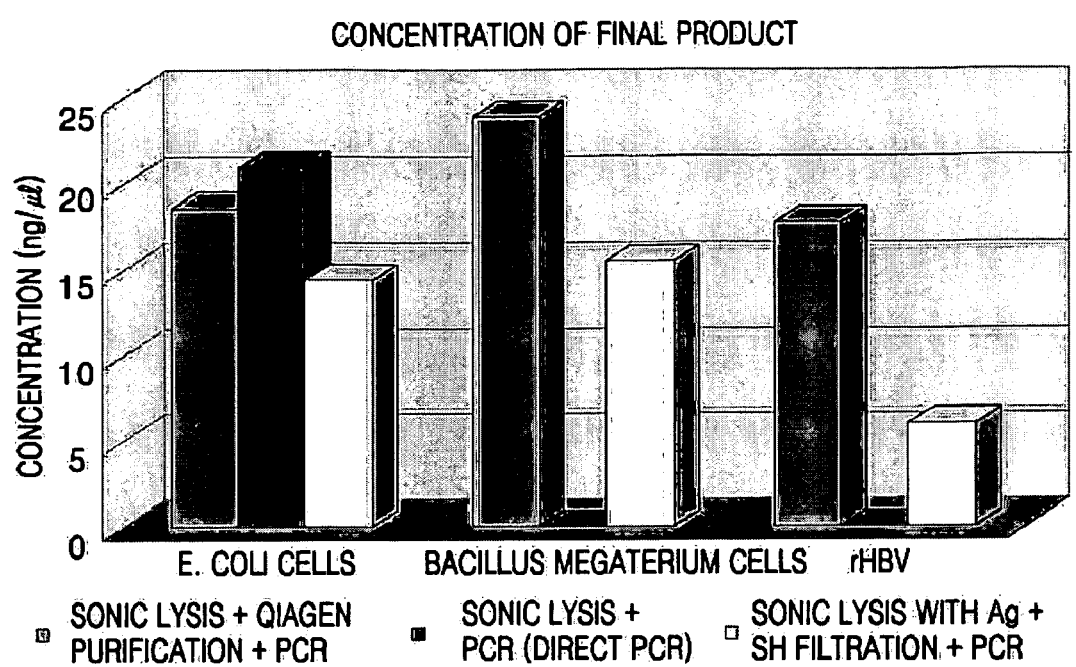
FIG. 3 illustrates a graph of concentrations (ng/μl) of the final PCR products, after isolating nucleic acids from *E. coli* cells, *Bacillus megaterium* cells, and recombinant hepatitis B virus (rHBV) using various purifying methods.

FIG. 3 is a graph of concentrations (ng/μl) of the final PCR products after isolating nucleic acids from *E. coli* cells, *Bacillus megaterium* cells, and recombinant hepatitis B virus (rHBV) using various purifying methods. The bars represent the amplified DNA concentrations (ng/μl). The *E. coli* cells having rHBV ($8 \times 10^2$~$8 \times 10^3$ cells/μl) were treated with sound waves (>500 Hz, 1 minute) and 100 ppm of silver nanoparticles were added to the cells. Nucleic acids were obtained in three ways: purifying the nucleic acids by using a Qiagen purification kit without using cell lysis, directly taking the sample without purification, or purifying using SH filtration. Then, the respective nucleic acids were amplified using PCRs. As a result, it was confirmed that the PCRs were successfully performed regardless of the purification method used. Since the purification method according to an embodiment of the present invention which includes SH filtration is simpler and less time-consuming than the other two methods performed, it can be more efficiently applied to isolation of the *E. coli* cells for realization of the LOC.

Example 4

Purification of Nucleic Acid of *Bacillus megaterium* Cell Using Silver Nanoparticles and Sound Waves To confirm whether a purification method according to an embodiment of the present invention can be applied to manufacturing samples for detecting gram positive bacteria, nucleic acids were purified from *Bacillus megaterium* cells and subjected to PCRs.

*Bacillus megaterium* cells ($6.5 \times 10^2$~$6.5 \times 10^3$ cells/μl) were treated with sound waves (1 minute) and 100 ppm of silver nanoparticles were added to the cells. Nucleic acids were obtained in three ways: purifying the nucleic acids by using a Qiagen purification kit, directly taking the sample without purification, or purifying using SH filtration.

The PCRs were performed in the same manner as in Example 3, except that primer C (SEQ ID No: 3) and primer D (SEQ ID No: 4) were used in place of primers A and B.

Referring to FIG. 3, the nucleic acid obtained directly after cell lysis using sound waves was not PCR amplified and the nucleic acid purified using the method according to an embodiment of the present invention was PCR amplified. The nucleic acid purified using the Qiagen purification kit, which was performed 1 minute after the cell lysis using sound waves, was PCR amplified with the highest yield among the three cases. It was confirmed that the purification method according to an embodiment of the present invention can remove proteins which function as PCR inhibitors. Although the present purification method has lower purification efficiency than the method of purifying using a chaotropic material, it is simpler and still less time-consuming than the other two cases, and thus, it can be more efficiently applied to a LOC which does not require a high degree of purification.

Example 5

Purification of Nucleic Acid of rHBV Using Silver Nanoparticles and Sound Waves

To confirm whether a purification method according to an embodiment of the present invention can be applied to manufacturing samples for detecting viruses, nucleic acids were purified from rHBV and subjected to PCRs. The PCRs were performed in the same manner as in Example 3

Referring to FIG. 3, the nucleic acid purified (15 minutes) using the Qiagen purification kit, after cell lysis using sound waves (1 minute), was PCR amplified with the highest yield without generating dimers. The nucleic acid obtained after cell lysis using sound waves (1 minute) was not PCR amplified. The nucleic acid purified (2 minutes) using the SH filtration after cell lysis using sound waves (1 minute), according to an embodiment of the present invention was PCR amplified. It was confirmed that when the purification was performed by adding the silver nanoparticles (100 ppm) to the virus sample, performing cell lysis, and then filtering the resultant product through the SH filter membrane according to an embodiment of the present invention, purification efficiency was somewhat lower than when the method of purifying using a Qiagen purification kit was used, but is simpler and less time-consuming.

In the method of purifying a nucleic acid using silver nanoparticles according to the present invention, PCR amplifiable DNAs can be purified in three processes, and is thus more rapid than the conventional methods. Thus, the present method can be very efficiently applied to the LOC.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of purifying a target substance comprising:
   mixing silver nanoparticles with a sample comprising the target substance and molecules having a thiol groups, wherein the target substance is a nucleic acid or a sugar, and the target substance does not have a thiol group;
   forming a complex of the molecules having the thiol group and the silver nanoparticles;
   removing the complex from the mixture; and
   obtaining a solution comprising the purified target substance.

2. The method of claim 1, wherein the sample comprises a cell or a virus, and the method further comprises lysing the cell or the virus.

3. The method of claim 2, wherein the lysing of the cell or the virus is performed using a method selected from the group consisting of mechanical grinding, a method using a chemical reaction, a method using an electrochemical reaction, a method using a biochemical substance, a method using ultrasonic waves, a method using sound waves, a method using microwaves, heating, a method using a laser, a method using electric field, and electrolysis.

4. The method of claim 1, wherein the silver nanoparticle complex is removed by passing the mixture through a structure having SH groups.

5. The method of claim 4, wherein the structure having SH groups is a glass fiber membrane modified with 3-(mercaptopropyl)trimethoxysilane.

6. The method of claim 1, wherein the silver nanoparticles have a size of 1-100 nm.

7. The method of claim 1, wherein the concentration of the silver nanoparticles is 10-1000 ppm.

8. The method of claim 7, wherein the concentration of the silver nanoparticles is 100-1000 ppm.

9. The method of claim 1, wherein the silver nanoparticles are directly added to the sample or generated by electrolysis using a silver electrode.

* * * * *